United States Patent [19]

Kronberg

[11] Patent Number: 5,413,596
[45] Date of Patent: May 9, 1995

[54] DIGITAL ELECTRONIC BONE GROWTH STIMULATOR

[75] Inventor: James W. Kronberg, Aiken, S.C.

[73] Assignee: The United States of America as represented by the United States Department of Energy, Washington, D.C.

[21] Appl. No.: 158,290

[22] Filed: Nov. 29, 1993

[51] Int. Cl.$^6$ .................................................. A61N 1/36
[52] U.S. Cl. ............................................................... 607/51
[58] Field of Search ............................... 607/50, 51, 52

[56] References Cited

U.S. PATENT DOCUMENTS

| | | | |
|---|---|---|---|
| 4,315,503 | 2/1982 | Ryaby et al. | 128/1.5 |
| 4,432,361 | 2/1984 | Christensen et al. | 128/419 |
| 4,454,883 | 6/1984 | Fellus | 128/422 |
| 4,548,208 | 10/1985 | Niemi | 128/419 |
| 4,561,426 | 12/1985 | Stewart | 128/1.5 |
| 4,574,809 | 3/1986 | Talish et al. | 128/419 |
| 4,674,482 | 6/1987 | Waltonen et al. | 128/1.5 |
| 4,911,686 | 3/1990 | Thaler | 600/14 |
| 5,014,699 | 5/1991 | Pollack et al. | 128/419 |
| 5,058,582 | 10/1991 | Thaler | 128/419 |
| 5,217,009 | 6/1993 | Kronberg | 128/419 F |

OTHER PUBLICATIONS

"The Friendly Fields of RF", *IEEE Spectrum*, Jun. 1985.

*Primary Examiner*—William E. Kamm
*Attorney, Agent, or Firm*—Brian R. Tumm; Harold M. Dixon; William R. Moser

[57] ABSTRACT

A device for stimulating bone tissue by applying a low level alternating current signal directly to the patient's skin. A crystal oscillator, a binary divider chain and digital logic gates are used to generate the desired waveforms that reproduce the natural electrical characteristics found in bone tissue needed for stimulating bone growth and treating osteoporosis. The device, powered by a battery, contains a switch allowing selection of the correct waveform for bone growth stimulation or osteoporosis treatment so that, when attached to the skin of the patient using standard skin contact electrodes, the correct signal is communicated to the underlying bone structures.

20 Claims, 2 Drawing Sheets

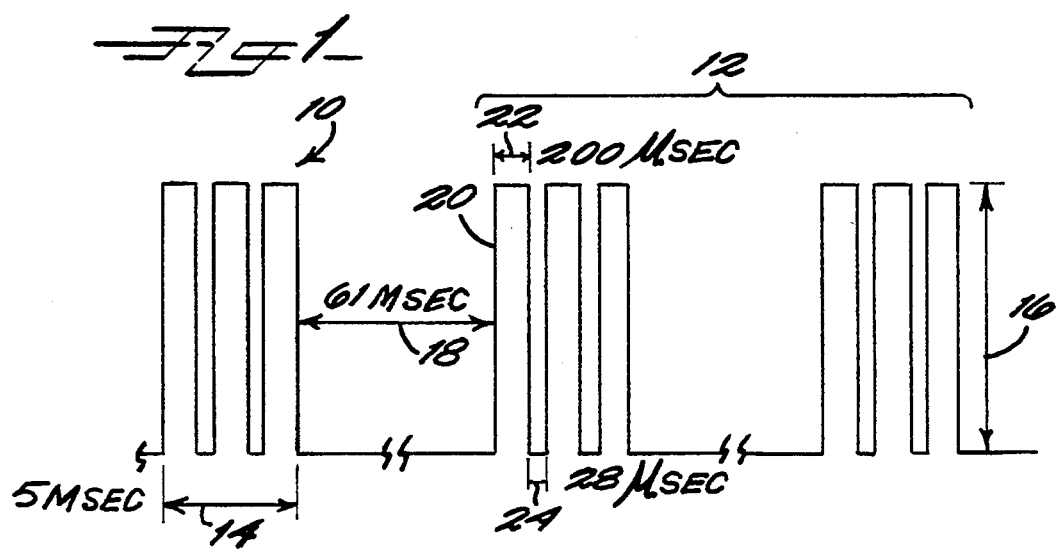
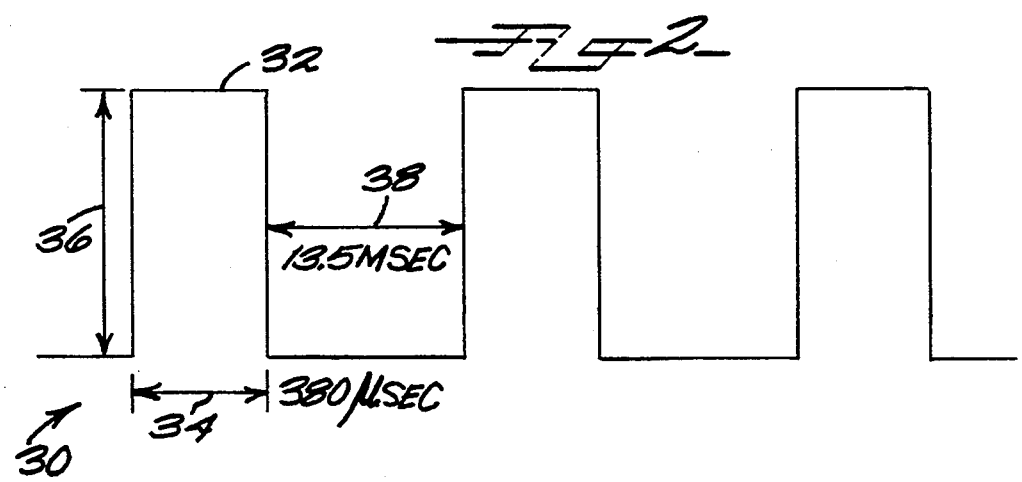
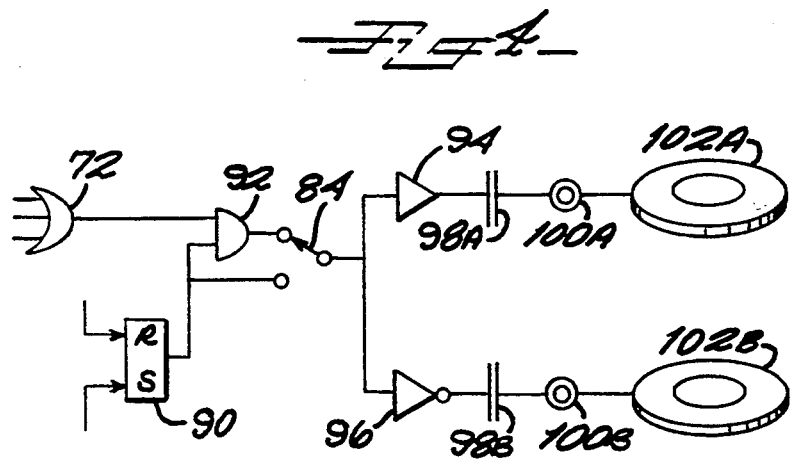

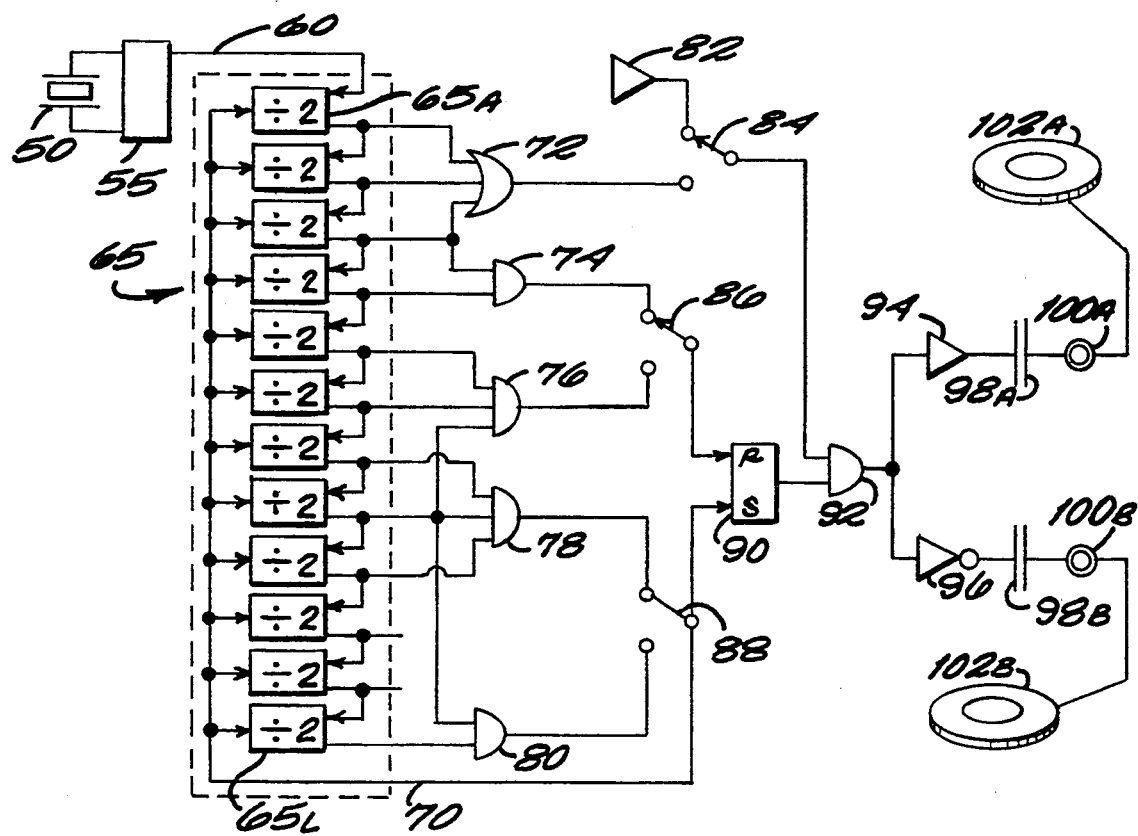
_Fig_3_
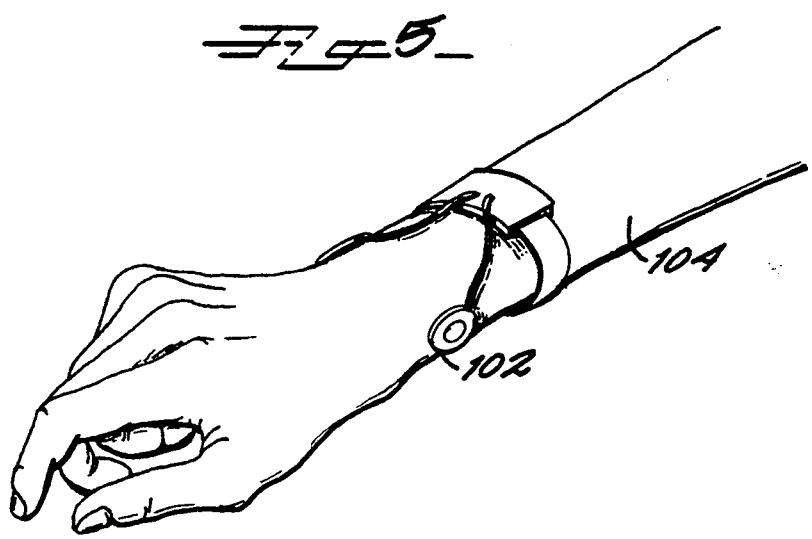
_Fig_5_

DIGITAL ELECTRONIC BONE GROWTH STIMULATOR

The United States Government has rights in this invention pursuant to Contract No. DE-AC09-89SR18035 between the U.S. Department of Energy and the Westinghouse Savannah River Company.

BACKGROUND OF THE INVENTION

1. Field of the Invention

The present invention relates to the electrical treatment of biological tissue. In particular, the present invention discloses a device that produces discrete electrical pulse trains for treating osteoporosis and accelerating bone growth.

2. Discussion of Background

Human bone is a combination of organic and mineral components; the chief mineral present is hydroxyapatite, a complex calcium phosphate ($Ca_5(PO_4)_3OH$) in crystalline form. Hydroxyapatite is piezoelectric; that is, it generates an electric charge when mechanically stressed. The electric signals generated by hydroxyapatite under stress, sometimes referred to as "bone talk", are detected by nearby bone cells, stimulating them to increase the production of hydroxyapatite. This increase in production of hydroxyapatite due to "bone talk" appears to be part of a feedback mechanism causing bone to be strengthened automatically at points of stress concentration. This feedback mechanism is weakened or interrupted in areas surrounding a bone fracture since stress concentrations at the fracture are typically nil.

A similar feedback mechanism seems to control the mineral content of intact bone. When normal "bone talk" is no longer communicated to surrounding cells, the production of hydroxyapatite decreases and osteoporosis (meaning "brittle bones") can result. Restoration of the piezoelectric signal can slow or reverse this condition.

It has long been known that the application of electric currents could speed bone growth and repair, but it was not until the 1960's that the weak signals generated by the bone itself were measured, analyzed, stimulated, and used to aid in healing. Studies conducted by C. A. L. Basset and others resulted in the identification of optimum waveforms which essentially duplicate the electrical characteristics of normal "bone talk".

FIG. 1 shows the optimum waveform which replicates normal "bone talk" instrumental in healing fractured bones. A series of pulses 10 consists of pulses 12 with pulse width 14 (5 msec), amplitude 16, and pulse interval 18 (61 msec) for a frequency of about 15 Hz. Each pulse 12 contains subpulses 20 with subpulse width 22 (200 $\mu$sec) and subpulse interval 24 (28 $\mu$sec) for a frequency of about 4400 Hz. A waveform used for treatment of osteoporosis, shown in FIG. 2, consists of a series of pulses 30, with pulses 32 of pulse width 34 (380 $\mu$sec), amplitude 36, and pulse interval 38 (13.5 msec) for a frequency of about 72 Hz.

While it was initially thought that synthetic "bone talk" signals would have to be relatively strong if applied from outside the body, it now seems that a threshold effect is involved. It has been found that alternating current signals billions of times more powerful than Bassett-type signals have virtually no greater effect on the healing rate of fractured bones than do their weaker counterparts. In addition, non-Bassett type alternating current signals may be used, but such signals generally require much higher power levels for equal effectiveness. Furthermore, the use of direct current signals is itself undesirable because they can result in electrolytic tissue damage and, if the signal strength is too great, actually destroy bone structure.

Optimum waveforms, generated by alternating current signals, can nearly double the rate of bone healing in ordinary fractures, and restart healing in nonunion fractures, i.e. those fractures in which normal healing has stopped without rejoining the pieces of the broken bone. The conventional treatment of non-union fractures involves surgical procedures which are often unsuccessful and invariably increases both the discomfort and expense incurred by the patient. The use of electronic stimulation as a method of treating fractured bones has reduced the reliance on conventional surgery.

Medical uses of electrical stimulation have been limited, possibly due to a belief that only high powered external signals will be effective. Direct transmission of high powered signals through the skin is harmful, potentially causing burn-like electrolytic damage. One alternative, electrode implantation below the skin, requires surgery. Such invasive procedures bring additional stress to the patient and, because of the possibility of infection, require ongoing medical attention. Also, such electrodes will require continuing adjustment since the current will be concentrated near the electrodes rather than being evenly distributed throughout the afflicted area.

As a result of limitations in present design, most modern work in electrical bone growth stimulation has been through the use of induction coils. See Niemi (U.S. Pat. No. 5,548,208). Radio-frequency (R.F.), signals applied to these coils, which are placed against the skin or on a plaster cast, induce signals of similar form in bone and other tissue. This method is non-invasive, simplifies patient care, and has the advantage of transmitting A.C. signals while D.C. signals are blocked. However, induction coil type stimulation is very ineffective at low "bone talk" frequencies. As a result, elaborate circuit modifications such as deliberate distortion or frequency modulation are required to approximate natural "bone talk" frequencies. Alternatively, circuit simplicity can be retained at the cost of an added power drain by using non-Bassett type signals such as sine waves.

Coils, high-frequency generators, modulating and driving circuitry all add to the weight, bulk, cost and power requirements of the signal generator. Generators now in use typically cost several thousand dollars each. Nominally "portable" equipment is driven by heavy, rechargeable battery packs with limited capacity while stationary devices require connection to A.C. power. The limitations of using existing stimulators require intermittent use by patients, typically for three to eight hours a day. Some models include circuitry to monitor use and insure patient compliance, but such circuitry increases the cost of the equipment. To ensure proper field distribution and adequate signal penetration into the bone, induction coils must frequently be custom made to fit the patient, thereby requiring adjustments to the signal generator. These modifications also add to cost and often delay the beginning of treatment.

Therefore, there is a present need for an electrical bone growth stimulator that generates Bassett-type signals, comparable to the pulse trains shown in FIG. 1 and FIG. 2. Such stimulator should be lightweight, compact, fully self-contained, inexpensive to manufacture and maintain, safe for unsupervised home use, and require no external coils or battery packs.

SUMMARY OF THE INVENTION

According to its major aspects and broadly stated, the present invention consists of an electrical circuit configuration capable of generating Bassett-type waveforms shown in FIG. 1 and FIG. 2, with alternative signals provided (switch selectable or through replaceable modules) for the treatment of either fractured bones or osteoporosis. The signal generator comprises a quartz clock, an oscillator circuit, a binary divider chain, and a plurality of simple, digital logic gates. Signals are delivered efficiently, with little or no distortion, and uniformly distributed throughout the area of injury. Preferably, power is furnished by widely available and inexpensive radio batteries, needing replacement only once in several days.

The present invention can be affixed to a medical cast without a great increase in either weight or bulk. Also, the disclosed stimulator can be used to treat osteoporosis or to strengthen a healing bone after the cast has been removed by attaching the device to the patient's skin or clothing. For example, the present device may be combined with the functions of a digital watch to strengthen a fractured wrist.

An important feature of the present invention is the integration of simple, digital, electrical components for producing pulse trains that accurately replicate normal "bone talk". As a result, the present invention can be fabricated onto a single logic chip, thereby reducing the size and cost of assembly.

Another feature of the present invention is that it can be used in conjunction with readily available skin contact electrodes. Electrodes made from a "hydrogel," a soft sticky gel containing water and dissolved mobile ions, are widely available and are used, for instance, in transcutaneous electronic nerve stimulation (TENS) to help relieve chronic pain. These electrodes can be used without modification in the present invention and can be affixed to the patient's clothing or directly on the skin. The present invention, in combination with skin contact electrodes, allows site-specific, distortion-free, low level, alternating current, pulse trains to reach an afflicted area. In addition, no high frequency modulation or deliberate counter-distortion is needed, thereby reducing the complexity and expense of treatment.

Still another feature of the present invention is the use of inexpensive low voltage batteries as a power source. This feature reduces the weight, size and the complexity of the device. Furthermore, the battery typically needs to be replaced only once a week and therefore results in a less expensive, less cumbersome treatment procedure, simplifying patient compliance. Electric shock is not a hazard since the generator has no connection to the alternating current (A.C.) powerlines, does not produce high voltages internally, and does not generate frequencies likely to induce heart fibrillation. Because of the threshold effect, only low power levels are required and therefore the equipment cannot produce a shock hazard even in the case of a malfunction. As a result, the present invention is completely safe for unsupervised home use.

Other features and advantages of the present invention will be apparent to those skilled in the art from a careful reading of the Detailed Description of a Preferred Embodiment presented below and accompanied by the drawings.

BRIEF DESCRIPTION OF THE DRAWINGS

FIG. 1 is a waveform used for the stimulation of bone tissue;

FIG. 2 is a waveform used for the treatment of osteoporosis;

FIG. 3 is an electrical schematic diagram of a pulsed signal generator according to a preferred embodiment of the present invention;

FIG. 4 is an electrical schematic diagram of a portion of an alternative embodiment of a circuit according to the present invention; and FIG. 5 is an illustration showing an application of the present invention.

DETAILED DESCRIPTION OF A PREFERRED EMBODIMENT

Referring now to FIG. 3, quartz crystal 50 is a standard, digital-clock crystal which oscillates at 32,768 Hertz, driven by, and controlling in turn, oscillator circuit 55. Oscillator output 60 thus consists of a sine, rectangular or other waveform at the same frequency, and thus with a 30.5 microsecond cycle time.

Oscillator output 60, oscillations, is used as the clock input to a twelve-stage binary divider chain 65 for counting the oscillations. Divider chain 65 generates a succession of twelve digital outputs 65(a) through 65(l), each taking the form of a square wave which lasts for an integral number of input cycles, such integers being successive powers of two. Divider chain 65 contains a reset input 70, which returns all outputs 65(a) through 65(l) to logic "zero" when chain 65 reaches its maximum count. Each digital output 65(a) through 65(l) of divider chain 65 therefore remains in the logic "zero" for a specified number of input cycles following a reset by reset input 70, switching to a logic "one" for the same number of cycles, and repeats this process indefinitely or until divider chain 65 is again reset to logic "zero".

Output signals 65(a) through 65(l) from divider chain 65, which each represent a count of oscillations, are combined by OR gate 72 and AND gates 74, 76, 78, 80, or by their equivalents constructed from simpler logic gates, to create signals corresponding to a sum of oscillations that in turn correspond to specific, predetermined numbers of oscillations having durations related to pulses and intervals of the Bassett "bone talk" waveforms.

OR gate 72 combines outputs 65(a), 65(b) and 65(c) to form a signal which remains at logic "one" for seven crystal-oscillator cycles and then goes to logic "zero" for one crystal-oscillator cycle, repeating this sequence indefinitely so long as the divider chain 65 is not reset. AND gates 74, 76, 78 and 80 perform AND functions using various outputs from divider chain 65 to produce outputs which are initially at logic "zero" after a reset by reset input 70 but change to logic "one" at 12, 176, 448 and 2176 cycles after the reset, respectively.

The outputs from OR gate 72 and buffer 82, which produces a constant "one" logic output and may be simply a connection to a positive supply, are tied to the input of a double-throw switch 84. Similarly the outputs of AND gates 74 and 76 are tied to the input of a double-throw switch 86. Outputs from AND gates 78 and 80 comprise the inputs of a double-throw switch 88. Switches 84, 86, and 88 operate in unison, thereby forming a three-pole, double throw switch. Alternatively, two-input signal multiplexers may be substituted for switches 154, 86 and 88.

When treating osteoporosis, the appropriate waveform is obtained from switch 84 selecting the signal from buffer 82, switch 86 selecting the signal from AND gate 74 and switch 88 selecting AND gate 78. For bone healing applications, switch 84 selects the signal from OR gate 72, switch 86 selects AND gate 76 and switch 88 selects AND gate 80. Alternatively, this circuit may be "hard wired," wherein unnecessary components are eliminated from the circuit to produce a less-expensive, single purpose circuit capable of either treating osteoporosis or of accelerating bone growth.

The signal chosen by switch 88 drives reset input 70 of divider chain 65, returning the count of divider chain 65 to zero. In osteoporosis treatment, divider chain 65 is reset to zero on count 448 cycles, while in fractured bone treatment reset to zero occurs at 2176 cycles. At the time divider chain 65 is reset to zero, the signal from switch 88 sets R-S flip-flop 90, making its output logic "one."

After a reset, divider chain 65 counts upward from zero. Switch 86 selects the output of either OR gate 72, which comes to logic "one" after twelve cycles, or that of AND gate 74, which comes to logic "one" after 176 cycles.

The combined action of switch 86 and 88 and R-S flip-flop 90 is thus a rectangular pulse train with a particular cycle duration and "one" time, depending upon the particular application. For treatment of osteoporosis, the duration is 13.7 milliseconds and the "on" time is 366 microseconds, whereas in fractured bone healing, these times are 66 milliseconds and five milliseconds, respectively.

Switch 84 selects either the constant logic "one" from buffer 82 or the cycling output from OR gate 72. AND gate 92 performs a logical AND between the selected signal from switch 84 and the output of R-S flip-flop 90. For osteoporosis treatment, the output from AND gate 92 is the same as the output from R-S flip-flop 90. With respect to bone healing applications, the output from AND gate 92 differs from the output of R-S flip-flop 90 in that the five millisecond logic "one" pulse is broken into 22 shorter, equal pulses of 214 microseconds each, separated by 30.5 microsecond intervals at logic "zero". Thus, AND gate 92 generates approximately the same outputs which Bassett and others have found optimum in the treatment of both osteoporosis and fractured bones. The exact pulse links and intervals do not seem to be critical and thus the outputs from gate 92, in which the Bassett intervals are approximated by multiples of 30.5 microsecond oscillation periods, should be equally effective in treatment.

The output of AND gate 92 is sent to a "push-pull" output amplifier consisting of buffer 94 and inverting buffer 96, which generate complementary output signals. Capacitors 98a and 98b provide electrical isolation and block any net direct current signal output component. Terminals 100a and 100b are made compatible with ordinary transcutaneous electronic nerve stimulation (TENS) devices or similar inexpensive skin contact electrodes 102 to facilitate connection between the circuit and the area of the body to be treated. FIG. 5 shows skin contact electrodes 102 affixed to patient's arm 104.

An alternative embodiment of the present invention is shown in FIG. 4, wherein one input of AND gate 92 is connected to the output of R-S flip-flop 90 and the other input is connected directly to the output of OR gate 72, thereby eliminating buffer 82. With this embodiment, the output of AND gate 92 is a constant train of 214-microsecond pulses separated by 30.5 microsecond intervals. For bone healing applications, switch 84 would select the output of AND gate 92, whereas for osteoporosis treatment, the output from R-S flip-flop 90 would be selected directly, thereby bypassing AND gate 92. The output of switch 2 would be used to drive buffer 94 and inverting buffer 96 directly.

It will be apparent to those skilled in the art of digital logic that various modifications and substitutions can be made in the preferred embodiment of the present invention, without departing from the spirit and scope of the present invention which is defined by the appended claims.

What is claimed is:

1. A device for generating an electrical signal for stimulating bone tissue under the skin of a person, said device for use with a power source and electrodes, said device comprising:

means for producing oscillations, said oscillating means producing said oscillations when said device is in electrical connection with said power source;

means for counting said oscillations, said counting means repeatedly and sequentially counting at least two groups of oscillations, each group of said at least two groups of oscillations including a number of oscillations, and, when said number counted by said counting means corresponds to a preselected number for said each group, said counting means issuing an output signal, said output signal varying in amplitude for said each group of said at least two groups so that said output signal represents a waveform, said waveform selected to stimulate bone tissue; and output means for transmitting said waveform to said electrodes to stimulate said bone tissue.

2. The device as recited in claim 1, wherein said means for producing oscillations further comprises:

an oscillator circuit; and a quartz crystal in operational connection with said oscillator circuit.

3. The device as recited in claim 1, wherein said means for counting said oscillations further comprises:

a binary divider chain having a plurality of outputs, each output of said plurality of outputs representing a count of oscillations; and means for combining at least two outputs of said plurality of outputs to produce an output corresponding to the sum of said counts of oscillations represented by said at least two outputs.

4. The device as recited in claim 1, wherein said counting means counts a first group of oscillations and a second group of oscillations, and said counting means further comprises:

a binary divider chain having a plurality of outputs, each output of said plurality of outputs corresponding to a count of oscillations;

first means for combining counts to produce a first number corresponding to a first sum of oscillations of at least two outputs of said plurality of outputs, said first combining means producing a first output signal when said first number corresponds to a first preselected number; and second means for combining counts to produce a second number corresponding to a second sum of oscillations of at least two outputs of said plurality of outputs, said second combining means producing a second output signal different from said first output signal when said second number corresponds to a second preselected number.

5. The device as recited in claim 1, wherein said waveform is selected to replicate the piezoelectric signal generated by hydroxyapatite, ($Ca_5(PO_4)_3OH$), of bone tissue.

6. The device as recited in claim 1, wherein said waveform has a pulse width of approximately 5 msec, an interval of approximately 61 msec, a subpulse width of approximately 200 $\mu$sec, and a subinterval of approximately 28 $\mu$sec.

7. The device as recited in claim 1, wherein said waveform has a pulse width of approximately 380 $\mu$sec and an interval of approximately 13.5 msec.

8. The device as recited by claim 1, wherein said output means further comprises:
means for removing direct electrical current from said waveform; and
means for amplifying said waveform.

9. A device for generating an electrical signal for stimulating bone tissue under the skin of a person, said device for use with a power source, said device comprising:
means for producing oscillations, said oscillating means producing said oscillations when said device is in electrical connection with said power source;
means for counting said oscillations, said counting means repeatedly and sequentially counting at least two groups of oscillations, each group of said at least two groups of oscillations having a number of oscillations, and, when said number counted by said counting means corresponds to a preselected number for said each group, said counting means issuing an output signal, said output signal varying in amplitude for said each group of said at least two groups so that said output signal represents a waveform, said waveform selected to stimulate bone tissue;
at least two electrodes; and
output means for transmitting said waveform from said counting means to said electrodes to stimulate said bone tissue.

10. The device as recited in claim 9, wherein said oscillating means further comprises:
an oscillator circuit; and
a quartz crystal in electrical connection with said oscillator circuit.

11. The device as recited in claim 9, wherein said means for counting said oscillations further comprises:
a binary divider chain having a plurality of outputs, each output of said plurality of outputs corresponding to a count of oscillations; and
means for combining at least two outputs of said plurality of outputs to produce an output corresponding to the sum of said counts of oscillations represented by said at least two outputs.

12. The device as recited in claim 9, wherein said counting means counts a first group of oscillations and a second group of oscillations, and said counting means further comprises:
a binary divider chain having a plurality of outputs, each output of said plurality of outputs corresponding to a count of oscillations;
first means for combining counts to produce a first number corresponding to a first sum of oscillations of at least two outputs of said plurality of outputs, said first combining means producing a first output signal when said first number corresponds to a first preselected number: and
second means for combining counts to produce a second count corresponding to a second number of oscillations of at least two outputs of said plurality of outputs, said second combining means producing a second output signal different from said first output signal when said second number corresponds to a second preselected number.

13. The device as recited in claim 9, wherein said waveform is selected to replicate the piezoelectric signal generated by hydroxyapatite, ($Ca_5(PO_4)_3OH$), of bone tissue.

14. The device as recited in claim 9, wherein said waveform has a pulse width of approximately 5 msec, an interval of approximately 61 msec, a subpulse width of approximately 200 $\mu$sec, and a subinterval of approximately 28 $\mu$sec.

15. The device as recited in claim 9, wherein said waveform has a pulse width of approximately 380 $\mu$sec and an interval of approximately 13.5 msec.

16. The device as recited in claim 9, wherein said output means further comprises means for removing direct electrical current from said waveform.

17. A device for generating an electrical signal for stimulating bone tissue under the skin of a person, said device for use with a power source and a plurality of electrodes, said device comprising:
means for generating oscillations;
a binary divider chain receiving said oscillations from said generating means, said binary divider chain having a plurality of outputs, each output corresponding to a count of oscillations;
binary logic gates in electrical connection with said binary divider chain, said binary logic gates combining counts to produce a first waveform and a second waveform,
said first waveform selected for stimulating bone growth, said second waveform selected for treating osteoporosis,
said first waveform and said second waveform each characterized by repeating series of amplitude changes, each change of said amplitude changes initiated by said binary logic gates when said binary logic gates have counted to a preselected number of oscillations since a previous amplitude change;
means in electrical connection with said binary logic gates for selecting alternatively said first and said second waveform, said selecting means having a first position for selecting said first waveform and a second position for selecting said second waveform; and
output means for transmitting said first and said second waveforms from said binary logic gates to said electrodes to stimulate said bone tissue.

18. The device as recited in claim 17, wherein said oscillating means further comprises:
a quartz crystal; and
an oscillator circuit, and wherein said power source is a portable battery.

19. The device as recited in claim 17, wherein said first and said second waveforms replicate piezoelectric signals generated by hydroxyapatite, ($Ca_5(PO_4)_3OH$) present in said biological tissue.

20. The device as recited in claim 17, wherein said first waveform has a pulse width of approximately 5 msec, an interval of approximately 61 msec, a subpulse width of approximately 200 $\mu$sec, and a subinterval of approximately 28 $\mu$sec and wherein said second waveform has a pulse of approximately 380 $\mu$sec and an interval of approximately 13.5 msec.

* * * * *